US00PP11038P

United States Patent [19]

Benarcik, Jr.

[11] Patent Number: Plant 11,038

[45] Date of Patent: Aug. 24, 1999

[54] HYDRANGEA PLANT NAMED 'FIREFLY'

[76] Inventor: Daniel B. Benarcik, Jr., 1714 N. Scott St., Wilmington, Del. 19806

[21] Appl. No.: 08/963,430

[22] Filed: Nov. 3, 1997

[51] Int. Cl.[6] ..... A01H 5/00

[52] U.S. Cl. ..... Plt./250

[58] Field of Search ..... Plt./67.1, 250

[56] References Cited

PUBLICATIONS

Huxley et al. (Eds.) "Hydrangea petiolaris", The New RHS Dictionary of Gardening, The Stockton Press New York. Vol. 2 pp. 610, 1992.

*Primary Examiner*—Howard J. Locker
*Assistant Examiner*—Melissa L. Kimball
*Attorney, Agent, or Firm*—C. A. Whealy

[57] ABSTRACT

A new and distinct cultivar of Hydrangea plant named 'Firefly', characterized by its unique and stable yellow and green variegated foliage; variegated leaf margins; and upright and climbing plant growth habit.

2 Drawing Sheets

The present invention relates to a new and distinct cultivar of climbing Hydrangea plant, botanically known as *Hydrangea petiolaris,* and hereinafter referred to by the cultivar name Firefly.

The new cultivar is a spontaneous mutation of a unidentified solid green-leaf *Hydrangea petiolaris.* The new cultivar was discovered and selected by the inventor in a controlled environment in Wilmington, Del., in 1992, as a single plant with variegated leaves including a variegated margin within a population of about 1,000 solid-green leaf plants. This single plant was selected based on this unique variegation. Asexual reproduction of the new cultivar by terminal cuttings taken at Wilmington, Del., has shown that the unique features of this new Hydrangea are stable and reproduced true to type in successive generations of asexual reproduction.

The following traits have been repeatedly observed and are determined to be the unique characteristics of 'Firefly'. These characteristics in combination distinguish the new Hydrangea as a new and distinct cultivar:

1. Unique and stable yellow and green variegated foliage.
2. Serrated leaf margins.
3. Upright and climbing plant growth habit.

The new Hydrangea has not been observed under all possible environmental conditions. The phenotype may vary significantly with variations in environment such as temperature and light level, without, however, any variance in genotype.

BRIEF DESCRIPTION OF THE PHOTOGRAPHS

The accompanying colored photographs illustrate the overall appearance and leaf variagation colors of the new Hydrangea, showing the colors as true as it is reasonably possible to obtain in colored reproductions of this type.

The photograph on the first sheet comprises a top perspective view of a typical plant of the new Hydrangea grown in a landscape setting.

The photograph at the top of the second sheet is a close-up view of typical leaves of plants grown in full sunlight.

The photograph at the bottom of the second sheet is a close-up view of typical leaves of plants grown in shade. Foliage colors in the photographs may appear different from the actual colors due to light reflectance.

DETAILED BOTANICAL DESCRIPTION

The following observations, measurements, values, and comparisons describe plants grown in Wilmington, Del., grown under full sunlight and shade in outdoor conditions during the summer. In the following description, color references are made to The Royal Horticultural Society Colour Chart except where general terms of ordinary dictionary significance are used.

Botanical classification: *Hydrangea petiolaris* cultivar Firefly.

Parentage: Spontaneous mutation of a unidentified solid green-leaf *Hydrangea petiolaris.*

Propagation:

*Type cutting.*—Terminal cuttings.

*Time to initiate roots.*—About 30 days at ambient temperatures of 27° C.

*Time to develop roots.*—About 40 days at ambient temperatures of 27° C.

Emerging aerial roots in the spring are fleshy and harden off to become dry brown which facilitates surface attachment.

*Rooting habit.*—Thick, fleshy and well-branched.

Plant description:

*Form.*—Upright and climbing plant form; initial upright growth does not require staking, however with subsequent growth, the aforementioned aerial roots provide primary support; initially basal lateral shoots grow horizontally until encountering a vertical surface upon which the aerial roots adhere and growth becomes upright; woody perennial.

*Branching habit.*—Removal of terminal apex will enhance branching.

*Lateral branches.*—Internode length: About 2.5 cm. Texture: Young lateral branches, glabrous; mature lateral branches, rough and peeling. Color: Young: 145A. Mature, woody: 174A.

*Foliage description.*—Leaves simple, generally symmetrical abundant, opposite, and flat in aspect. Size, largest leaves: Length: About 7 cm. Width: About 5.5 cm. Shape: Ovate. Apex: Acuminate. Base: Obtuse. Margin: Serrate. Texture: Smooth. Color: Yellow-green and green variegated leaves. Color will vary with amount of light. Actual shape and size of yellow-green and green areas is variable. Full sunlight: Upper surface: Yellow-green: 154A to 11A. Green: 147A/146A. Under surface: Yellow-green: 154A to 11A, dulled. Green: 147A/146A, dulled. Shade: Upper surface: Yellow-green: close to 154A. Green: 147A/146A. Under surface: Yellow-green: Close to 154A, dulled. Green: 147A/146A, dulled. Petiole: Size: Length: About 6 cm. Diameter: About 3 cm at base, about 2 cm at apex. Color: 154A.

Flower description: Typical of *Hydrangea petiolaris*. Flowers rarely observed; arranged in corymbs with about 10 to 15 white sterile outer flowers and numerous small off-white fertile flowers.

Disease resistance: Under commercial conditions, resistance to pathogens common to Hydrangea has not been observed.

It is claimed:

1. A new and distinct Hydrangea plant named 'Firefly', as illustrated and described.

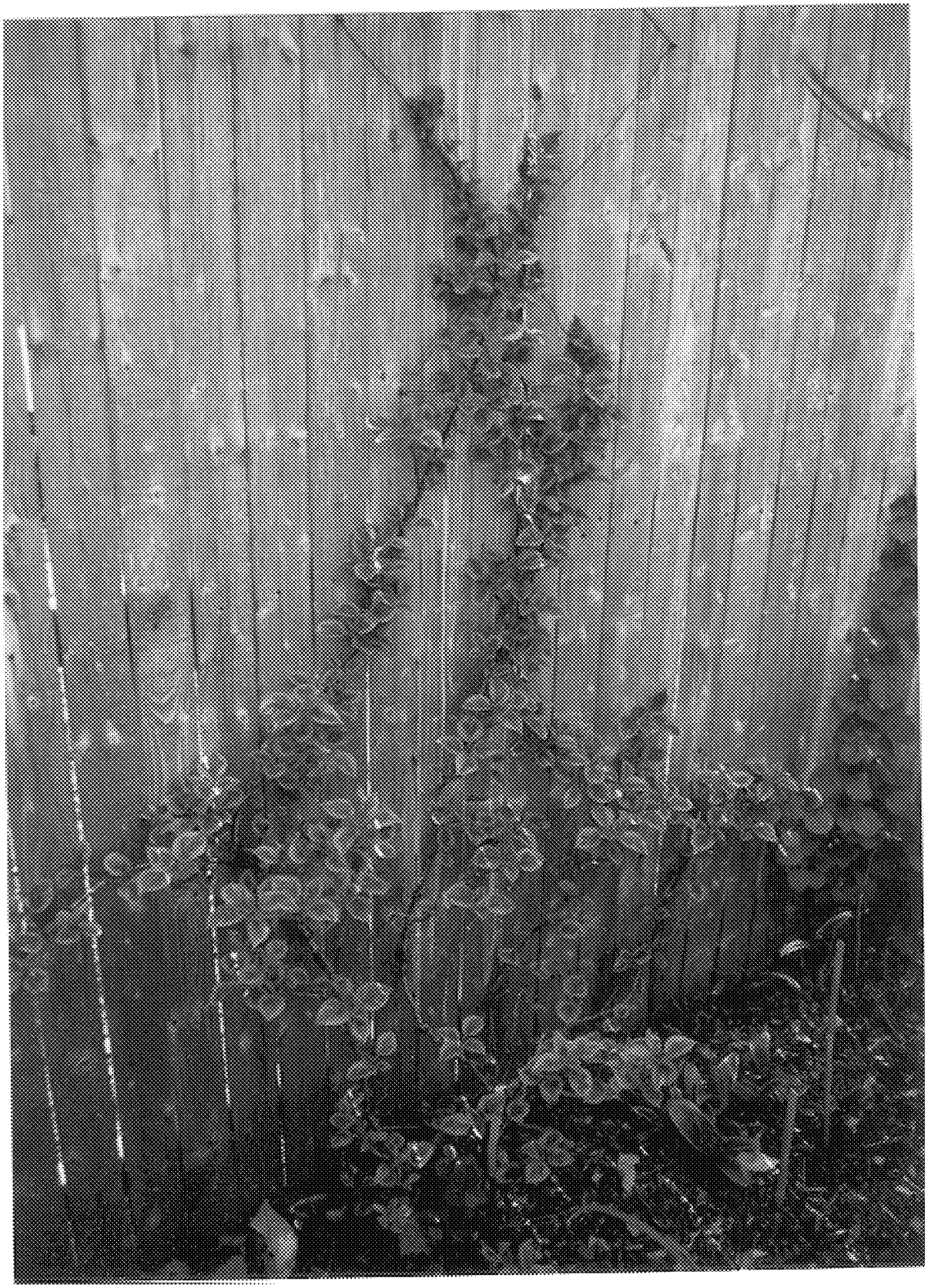

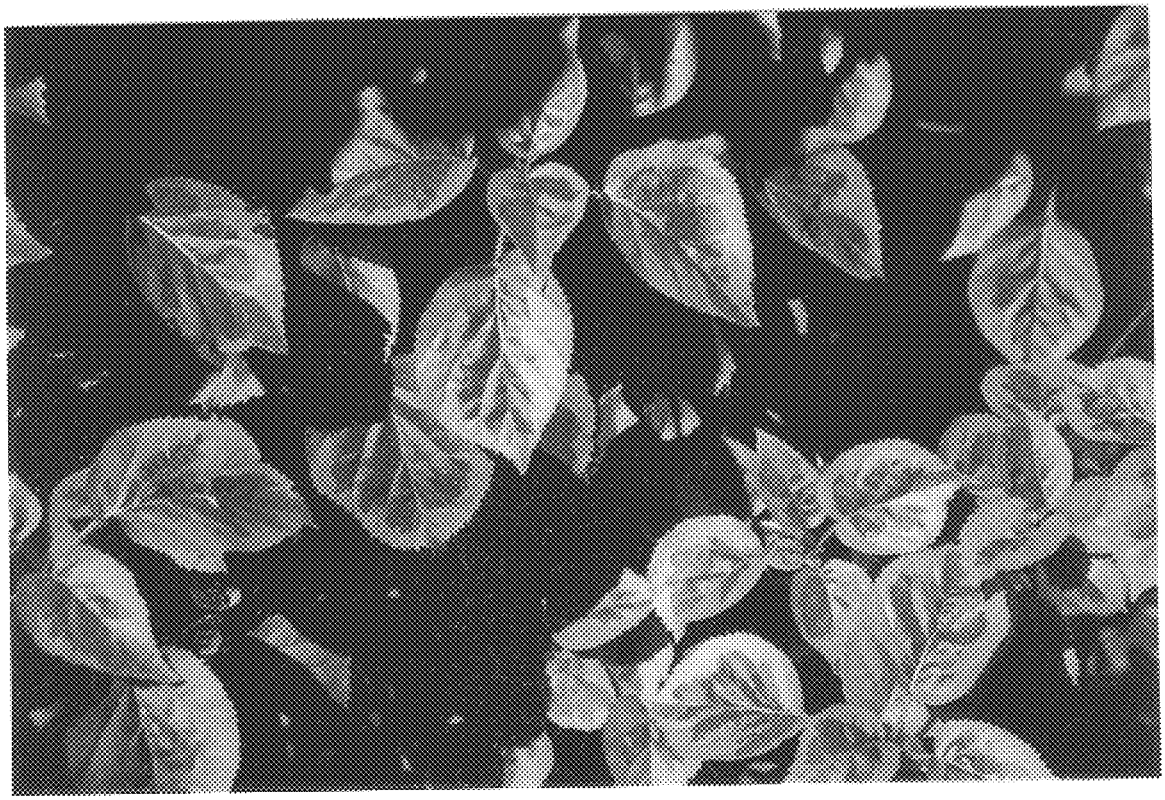
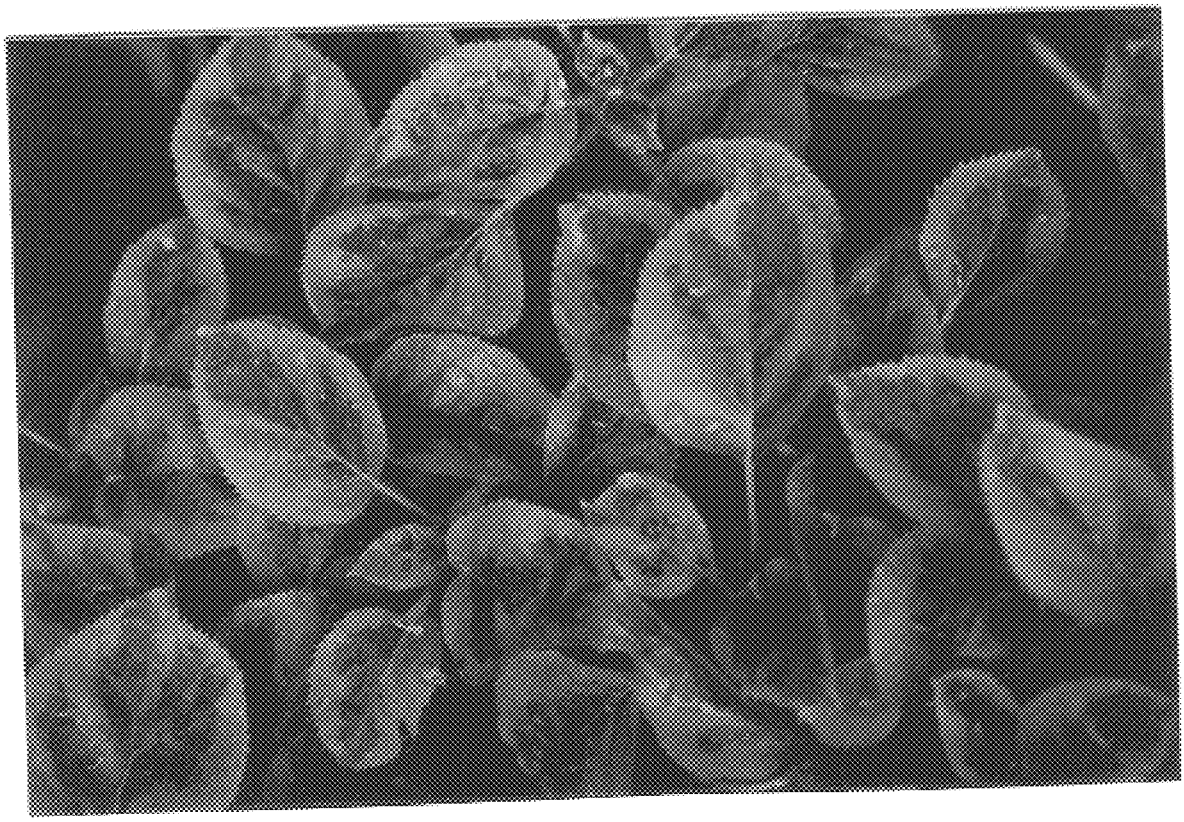

* * * * *